United States Patent [19]
Jacquot et al.

[11] Patent Number: 5,646,085
[45] Date of Patent: Jul. 8, 1997

[54] MATERIAL BASED ON TUNGSTEN CARBIDE(S), CATALYST AND PROCESS USEFUL FOR THE HYDROGENATION OF AN AROMATIC NITRO OR NITROSO DERIVATIVE EMPLOYING THIS CATALYST

[75] Inventors: Roland Jacquot, Sainte Foy les Lyon; Claude Mercier, Lyons, both of France

[73] Assignee: Rhone-Poulenc Chimie, Courbevoie, France

[21] Appl. No.: 272,288

[22] Filed: Jul. 8, 1994

Related U.S. Application Data

[62] Division of Ser. No. 955,196, Oct. 2, 1992, abandoned.

[30] Foreign Application Priority Data

Oct. 4, 1991 [FR] France ................... 91 12269
Oct. 4, 1991 [FR] France ................... 91 12270
Jul. 10, 1992 [FR] France ................... 92 08581

[51] Int. Cl.$^6$ .......................... B01J 27/22; C07C 209/00
[52] U.S. Cl. .......................... 502/177; 564/421
[58] Field of Search ................ 502/177; 564/421

[56] References Cited

U.S. PATENT DOCUMENTS

| | | | |
|---|---|---|---|
| 3,790,410 | 2/1974 | Mund et al. | 502/177 X |
| 4,522,708 | 6/1985 | Leclercq et al. | 502/177 X |
| 4,851,206 | 7/1989 | Boudart et al. | 502/177 X |
| 5,139,987 | 8/1992 | Ledoux et al. | 502/177 |

FOREIGN PATENT DOCUMENTS 1319442  12/1989  Japan ................... 502/177

OTHER PUBLICATIONS

Kinetics of the Liquid–Phase Hydrogenation of Aromatic Nitro–Compounds in the Presence of Tungsten Carbide Catalyst, György Horányi et al., Journal Of The Chemical Society, 8:827–829 (1975) no month available.

Selective Catalytic Behavior of Tungsten Carbide in the Liquid–Phase Hydrogenation of Organic Compounds, György Vértes et al., Journal Of The Chemical Society, 10:1400–1402 (1973) no month available.

Tungsten Carbide as a Catalyst for Liquid (aqueous) Phase Heterogeneous Catalytic Hydrogenation, Horányi et al., Chemical Abstracts, 78(25):159108y (1973) no month available.

Selective Catalytic Hydrogenation of Nitro Compounds and Quinones, Horányi et al., Chemical Abstracts, 81(7):37392c (1974) no month available.

Application of Tungsten Carbide and Tungsten Oxide in Liquid–Phase Catalytic Hydrogenation, Vértes et al., Chemical Abstracts, 81(8):41902m (1974) no month available.

Control of the Catalytic Activity of Tungsten Carbides. III. Activity for Ethylene Hydrogenation and Cyclohexane Dehydrogenation, Vidick et al., Chemical Abstracts, 106(25):213251b (1987) no month available.

*Primary Examiner*—Glenn A. Caldarola
*Assistant Examiner*—Elizabeth D. Wood
*Attorney, Agent, or Firm*—Finnegan, Henderson, Farabow, Garrett & Dunner, L.L.P.

[57] ABSTRACT

The present invention relates to a process and a catalyst for hydrogenation of aromatic nitro or nitroso (nitrosated) compounds. The process, useful in hydrogenation, especially in the liquid phase, of compounds, nitroaromatic ones in particular, is defined in that the said compound is hydrogenated in the presence of tungsten carbide, the partial pressure of hydrogen being at least equal to two atmospheres ($2 \times 10^5$ pascals). The process also has application to organic synthesis.

6 Claims, No Drawings

5,646,085

MATERIAL BASED ON TUNGSTEN CARBIDE(S), CATALYST AND PROCESS USEFUL FOR THE HYDROGENATION OF AN AROMATIC NITRO OR NITROSO DERIVATIVE EMPLOYING THIS CATALYST

This application is a division of application Ser. No. 07/955,196 filed Oct. 2, 1992, now abandoned.

TECHNICAL FIELD OF INVENTION

The present invention relates to a process for hydrogenation of aromatic nitro or nitroso (nitrosated) compounds. It relates more particularly to the preparation of halogenated amines from halogenated aromatic nitro compounds and especially to amines para-substituted by OH, Cl, Br, F, alkoxy or acyloxy on the hydroxylamine intermediate by Bamberger rearrangement.

BACKGROUND OF THE INVENTION

When a hydrogenation process is applied to an aromatic nitro compound carrying halogen atoms bonded to the aromatic nucleus, the conversion of the nitro group to an amino group is invariably followed by hydrogenolysis of the carbon-halogen bond to give, on the one hand, the dehalogenated nucleus and, on the other hand, hydrogen halide acids. This phenomenon has been known for a very long time, since it was described by P. Sabatier and A. Mailhe in 1904.

Many studies have been conducted to avoid this secondary reaction while allowing the catalyst to remain properly active. These studies have led to various solutions which can be classified into two groups: those employing platinum or palladium and those employing Raney nickel as the hydrogenation catalyst. All these studies involve the use of a modified catalyst.

In the first group of techniques, those employing metals of the platinum group, are processes in which the hydrogenation catalyst employed is platinum deposited on carbon, optionally inhibited by the presence of an adjuvant referred to by the neologism "selectivity agent", such as thioethers and disulfides. Although the degree of dehalogenation is very low, this technique still presents numerous disadvantages, including the formation of highly toxic byproducts such as diazo derivatives, and the very high cost of the catalyst.

In the second group of techniques, those which employ the metals of the first row of group VIII and especially nickel in the form of Raney nickel, the manufacture of diazo derivatives is avoided, but the formation of other interfering products remains very high, especially the products resulting from hydrodehalogenation (hydrogenolysis of carbon-halogen bonds). Hydrogenolysis products are particularly troublesome in the manufacture of fluorinated anilines as it is not possible to separate fluorinated anilines from unsubstituted anilines at costs which are reasonable relative to the selling price of the said fluorinated anilines.

Thus, attempts have been made to make the hydrogenation reaction more selective by employing selective catalyst poisons, poisons which are referred to in this context as selectivity agents.

Thus, the use of Raney nickel to which a calcium or magnesium hydroxide is added as a selectivity agent has been recommended. In order to avoid dehalogenation, the reaction temperatures must be very moderate, and this does not allow these processes to be employed on an industrial scale.

It has also been proposed to employ Raney nickel in combination with thiocyanate, alkylamine, alkanolamine, a heterocyclic base, trialkyl phosphite, cyanamide or dicyandiamide. None of these improvements has neatly solved the problem, especially since it is easier to use a material which intrinsically offers the required qualities as a catalyst rather than a catalyst which has to be poisoned with sufficient adroitness so that it will catalyze only certain reactions and will do so, moreover, without losing most of its catalyst effectiveness in these reactions.

These difficulties are also encountered during the synthesis of anilides, especially of acylated amino compounds from the corresponding nitro derivatives (or, in a broader sense, in the synthesis of intermediates between the nitro derivatives and the anilines, whether identified or not).

In fact, during conventional syntheses of anilides it is often necessary to carry out the reduction and the amidation in several stages and it is necessary to employ powerful reactants such as anhydrides, or mixed anhydrides.

SUMMARY OF THE INVENTION

Thus, one of the objectives of the present invention is to provide a new process for the hydrogenation of a compound selected from the group consisting of nitro compounds and nitroso compounds, which process comprises subjecting said compound to a partial pressure of hydrogen equal to at least two atmospheres in the presence of tungsten carbide.

A further objective of the present invention is to provide a new process for the hydrogenation of halogenated aromatic nitro compounds, especially for the synthesis of halogenated anilines.

The halogenated, and more particularly fluorinated, nitro compounds are very sensitive to hydrolysis during hydrogenation, which releases two molecules of water per nitro functional group.

Thus, another objective of the present invention is to provide a new process for hydrogenation of halogenated aromatic nitro compounds, especially for the synthesis of halogenated anilines, which avoids the hydrogenolysis of the carbon-halogen bonds.

A further objective of the present invention is to provide a new process for hydrogenation and amidation of nitrogenous, generally nitrosated, aromatic compounds, especially for the synthesis of anilides, which permits an amidation which is virtually simultaneous with the formation of the aniline functional group (aniline is intended to mean any amine in which the amine functional group is directly bonded via the nitrogen to an aromatic nucleus) in the presence of the acid whose anilide is desired.

These objectives and others which will appear hereinafter are attained by means of a process which can be used for hydrogenation, especially in liquid phase, of compounds, nitroaromatic compounds in particular, where the said compound is hydrogenated in the presence of activated tungsten carbide, the partial pressure of hydrogen being equal to at least about two atmospheres (2×10 pascals).

Several decades ago, tungsten carbide stirred some hope in the field of hydrogenation catalysis because its utility range seemed different from that of other catalysts, especially those based on metals of group VIII. However, the results have not been equal to the hopes to which it gave rise. In fact, especially in liquid phase, the reaction is slow and sluggish and is not suited for industrial application. The various measures recommended in order to overcome this disadvantage, such as the use of high specific surfaces or doping with a metal of the platinum group have not given the expected results, while at the same time limiting the advantages of tungsten carbide, namely an activity range differing from that of the metals of the platinum group. Following this lack of success, the catalytic properties of tungsten carbide were no longer considered useful, except as laboratory curiosities.

Because of this low catalytic activity in liquid phase, the studies have been restricted to the reactions employed in petrochemistry for modifying hydrocarbons; especially to dehydrogenation reactions or to the synthesis of hydrocarbons from water gas.

Completely surprisingly, a study conducted by the present inventors, contrary to prejudices concerning the usability of tungsten carbide, has led to the conclusion that it is possible to obtain hydrogenation kinetics which are highly acceptable, provided that the work is done at sufficient partial pressures of hydrogen. In fact, above a hydrogen partial pressure threshold situated between 1.5 and 2 atmospheres, the reaction kinetics suddenly accelerate. (In the present description, one atmosphere is considered to be equivalent to the metric system unit of $10^5$ pascals.) At these pressures, the activation occurs very rapidly and the induction period is barely detectable. The phenomenon is general and has been verified for numerous grades of tungsten carbide and for numerous reactions.

As the term is used in this application, tungsten carbide is considered to be activated tungsten carbide as explained hereinafter.

As stated, the hydrogen partial pressure threshold is always above a value of between 1.5 and 2 atmospheres; clearly this threshold depends on the working conditions. When work is performed at temperatures greater than or equal to 150° C., the threshold is situated within the vicinity of 2 atmospheres.

When work is performed in a liquid medium that is acidic and reactive (said medium being homogeneous or heterogeneous and having an acid titre equalling at least 0.1N and preferably 1N), it is not necessary to increase the pressure much above 2 atmospheres in order to reach the threshold, and this can be done at a relatively low temperature (about 50° C.).

In other situations, there is always a threshold, although its value is more difficult to determine.

It is preferred that activation occur either at pressures higher than 10 (and preferably 20) atmospheres, and at a temperature higher than 100° C. (and preferably 150° C.); or at a temperature of at least 100° C. and at a pressure higher than 10 atmospheres.

It is possible, of course, to work at a pressure and/or temperature different from that of the activation. It is preferable, though, for work to be performed under conditions at which activation occurs.

In addition, the reaction can be conducted over a wide range of pressures and temperatures and according to numerous methods of implementation.

It can also be carried out batchwise, semicontinuously, or continuously, in a stirred reactor or in a fixed trickle bed or even in vapor phase.

In all cases there is a possibility of recovering and reusing the catalyst, and this adds to the advantage of the process.

Bearing in mind that the work is done under heterogeneous catalysis conditions, the subsequent recovery of the catalyst is very easy, since it can be performed by simple means such as filtration or decantation.

The quantity of catalyst to be employed is not critical and can vary within wide limits; from 0.01% to 50% by weight of catalyst is generally employed in relation to the quantity of substrate.

According to one of the preferred embodiments of the invention, the reaction is conducted in a solvent medium. It can also be conducted without any solvent, with the reactants acting as a solvent.

One of the advantages associated with the use of tungsten carbide lies in the remarkable chemical inertness of this material, especially towards protic reactants and especially strong protic acids. This characteristic is particularly advantageous in so-called Bamberger reactions. By way of example, some characteristics of this reaction can be recalled and can be exemplified in the following manner, by taking the case of nitrobenzene or nitrosobenzene

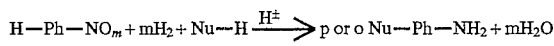

where Nu-H is a nucleophilic protic molecule (directly or through the intermediacy of its anion); Nu-H may be an acid or a protic compound such an alcohol or phenol or it may be water. The reaction takes place essentially at the para position to the nitro or nitroso functional group except when this position is occupied by a substituent whose nucleophilicity is substantially higher than that of Nu-H. In the case of other aromatic nuclei, Nu is grafted on positions which are equivalent to the ortho position and more generally to the para position. For further details on the Bamberger reaction, reference may be had to the abundant literature on this subject.

The reaction is proportionately better the more acidic the reaction mixture, and, especially, the more acidic the solvent. Bronsted, or even Lewis, acids can be employed.

To date, the catalysts employed have been chosen from those based on metals of the platinum group and hence, are expensive and liable to produce numerous toxic by-products such as azo compounds. They also exhibit an excessive sensitivity to sulfur, which is particularly troublesome in the case of nitro derivatives, which are generally obtained by reaction of nitric acid in a sulfuric acid medium and which are stabilized by addition of sulfur compounds.

Examples of acidic groups which can be employed for the reductions which are characteristic of a "Bamberger rearrangement", are the first acidic functional group of phosphoric acids, of sulphuric acid, and those of hydrogen halide acids and their mixtures, although these are generally employed pure.

Besides their character of teaching by example, the above acids are generally those most commonly utilized for Bamberger rearrangements.

The solvents which can be employed for the Bamberger reaction are the usual solvents for this purpose. It will be recalled in particular that protic or aprotic organic solvents can be employed, which can consist at least partially of Nu-H, containing at least organic or inorganic acid.

In general, the reaction is carried out in the absence of solvent or in a solvent chosen from water, alcohols, aromatic compounds and mixtures thereof. The solvent is advantageously chosen from protic solvents and preferably from water and alcohols, advantageously methanol and mixtures containing methanol.

The same considerations apply to the hydrogenation reaction without Bamberger rearrangement, the only difference being the presence of strong acid.

The temperatures used to conduct the reaction can vary within very wide limits.

It is thus possible to operate from room temperature, theoretically up to the boiling temperature of the solvent employed, care being taken nevertheless not to exceed temperatures at which the substrate and/or the product to be obtained could decompose. In practice, the work is generally done at temperatures between room temperature and 400° C., advantageously between 20° and 250° C., and preferably between 50° and 150° C.

In the liquid phase, the work is generally done at temperatures between room temperature and the boiling temperature of the reaction mixture under the operating conditions, advantageously between 20° C. and 200° C., and preferably between 50° and 150° C.

The reaction can be conducted preferably at autogenous pressure in a closed reactor of the autoclave type containing a hydrogen atmosphere. In the latter case, the partial pressure of hydrogen may range from 2 to 100 atmospheres and preferably from 5 to 20 atmospheres.

The reaction is preferably conducted with stirring, this being generally continued until the substrate has completely or virtually completely disappeared.

At the end of the reaction, the catalyst is separated from the reaction mixture by any physical means of separation known per se, such as, for example, filtration, decantation, elutriation or centrifugation.

The catalysts and/or the solvents thus recovered can then be recycled to the beginning of the process, either directly or following purification.

Another objective of the present invention is to provide a new tungsten carbide-based catalyst whose kinetic characteristics are significantly improved in relation to tungsten carbide.

This objective is obtained by subjecting tungsten carbide or a composite containing it to a treatment with hydrogen, or a compound that generates hydrogen under the conditions of the reaction, advantageously in liquid medium, at a temperature of at least 50° C., advantageously 100° C. and at a pressure of at least about 2 atmospheres, advantageously about 5 atmospheres, and preferably at about 10 atmospheres.

More specifically, the activation is preferably carried out by subjecting the tungsten carbide, or composite containing tungsten carbide, to a hydrogenation treatment at a temperature of at least 60° C. at a pressure of at least 20 atmospheres or a temperature of 100° C. at a pressure of at least 10 atmospheres or a temperature of 150° C. at a pressure of at least 2 atmospheres.

The upper values of pressure correspond to constraints of a practical nature. Purely by way of example, 100 atmospheres can be given as a practical upper limit of pressure.

A rounded off value of 300° C., preferably of approximately 250° C., can be given as an upper value of temperature.

This material can be employed especially as a hydrogenation catalyst for the reduction of nitroaromatic and nitrosoaromatic compounds. When the substitutions lend themselves to it, they permit the various Bamberger reactions and do so all the more easily since the catalyst according to the invention withstands acidic conditions very well.

The catalyst can take the form of a monolithic substrate (honeycomb or the like) made of tungsten carbide, or of a monolithic substrate coated with a layer of tungsten carbide, or can also take the form of divided products made of, or coated with, tungsten carbide. A divided form is intended to mean pulverulent products (powders) and also the articles obtained by forming these products (beads, tablets, pellets, granulates, extrudates, agglomerates, and others, of circular, oval, trilobar or multilobar section, solid or hollow). Catalysts of bead, tablet and other type offer the advantage of being capable of subsequently being very rapidly separated from the reaction mixture merely by decanting. Catalysts of pulverulent type generally require a filtration for their separation.

The above mentioned catalyst forms are chosen with a specific surface which is appropriate for the application being considered. In practice, it is possible to use a tungsten carbide whose specific surface as measured by the BET (Brunauer, Emmett and Teller) method, can vary from a tenth to several hundred or even one thousand or several thousand square meters per gram and in general from 1 to 500 m²/g.

It will be possible to use for this purpose either tungsten carbides available commercially or tungsten carbides which will have been synthesized by any process known per se. By way of example, tungsten carbides with high specific surfaces can be manufactured by the process described in Patent Application PCT/FR90/00204.

DESCRIPTION OF THE PREFERRED EMBODIMENTS

Tungsten carbides in which the tungsten/carbon ratio is in the region of 1, denoted by WC, are preferred. Advantageously, the process applies to the nitro compounds corresponding to the formula (I):

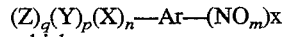

in which

Ar denotes a mono- or polycyclic, homo or heterocyclic, aromatic radical optionally substituted by an alkyl group containing 1 to 4 carbon atoms, an aralkyl or alkenyl group, or a functional group such as hydroxyl, trifluoromethyl, nitrile, acid, ester, ketone, an unsaturated acid, ether, or heterocyclic ring;

X, Y and Z denote a halogen chosen from fluorine, chlorine and bromine;

x denotes an integer from 1 to 3;

n, p and q denote an integer from 0 to 5 it being possible for the sum n+p+q to be equal to or greater than 0; and m is 1 or 2.

Ar preferably denotes a monocyclic aromatic radical, X and Y represent chlorine or fluorine, q is 0 and the sum of n+p is from zero to 3. Most preferably, Ar denotes a monocyclic, homocyclic aromatic radical, X and Y represent chlorine or fluorine, q is 0 and the sum n+p is from 1 to 3.

When employed for an at least partial amidation of the aniline which is being formed, the process is directed, in addition to those specified above, to those compounds of the following formula where Ar is $Ed_rAr'$:

where Ed denotes one or a number of similar or different groups, such as, e.g., alkyl groups containing 1 to 4 carbon atoms, an aralkyl or an alkenyl group, or a functional group such as hydroxyl, trifluoromethyl, nitrile, acid, ester, ketone, unsaturated acid, ether, or heterocyclic ring, and where r is an integer from 0 to 3, advantageously chosen from 0, 1 or 2. Where m is 1 or 2, Ar' and x have the values shown above.

Thus, Ar' is a mono or polycyclic aromatic radical, either homo or heterocyclic, which is optionally substituted. For both Ar and Ar', the number of rings is preferably equal to 5 at most, and more preferably 3.

The reaction is particularly interesting for molecules wherein Ed is alcoxyl, acyloxyl, and hydroxyl.

In fact, the different Ed do not significantly alter the operability of the reaction. Yet these groups are of interest since the tungsten carbides make possible a surprising selectivity of the hydrogenation of the nitro group in relation to the Ed group. It should also be pointed out that when the groups are electro-donors, the reactivity of the aniline function is increased. In the majority of situations, this results in many high molecular weight by-products. The same can be said of polynitro compounds having multiple nitro groups on the same nucleus, which result in well-known, extremely active polyanilines.

Finally, the hydrogenation of compounds carrying more than three nitro functions is also included in this invention, provided there are at most three nitro functions per ring.

Although the scope of derivatives that can be treated in this manner is extremely broad, it is best that these compositions be liquid in working conditions, or else be soluble in the reaction medium.

It is thus easier to manipulate compositions wherein the total carbon number equals 50 at most, and preferably 30.

When it is desired to run the amidation reaction, a mixture containing the acid whose amide it is desired to make is employed as a solvent. Besides this acid, it may contain water and an inert, preferably polar, solvent.

Sulfuric, sulfonic, phosphoric and, above all, carboxylic acids may be mentioned among the acids. It is preferable that the boiling point of these acids be higher than approximately 150° C.; if this is not the case, it will be necessary to accept working at a partial pressure of the said acid of more than one atmosphere ($10^5$ pascals). The reaction is well-suited to carboxylic acids, preferably monoacids, in which the number of carbons is from 1 to 30, preferably 2 to 20. This reaction is particularly advantageous for acids of low molecular weight, especially acetic acid. This reaction runs particularly well when the para or para-like positions are occupied by a substituent which is especially an electron donor. In particular, this substituent may be a phenol functional group or a derived functional group, ester or ether.

By way of guidance, the amidation reaction can in principle be used at a temperature of about 0° to 300° C. or more.

This amidation reaction generally takes place at high temperature, that is to say at a temperature significantly higher than 100° C. The temperature at which the amidation reaction commences depends on the substrate, the acid and the acid concentration. It can be easily determined by a person skilled in the art using routine tests, as long as the practitioner is aware of the existence of this amidation under nonconcomitant conditions of hydrogenation.

This amidation is generally virtually complete in the case of temperatures higher than or equal to 150° C. A reaction temperature of 150° C. to 250° C. is therefore preferably chosen.

This reaction is at the same time 1) very advantageous from the viewpoint of economy, because it makes it possible to employ relatively inexpensive reactants such as acids instead of various anhydrides (including the mixed anhydrides obtained by elimination of water between hydrogen halide acids and oxygen-containing acids which are, in fact, acid chlorides) and 2) very surprising from the scientific viewpoint. In fact, during the hydrogenations using tungsten carbide which were conducted previously, the work was restricted to relatively low temperatures, generally not exceeding 100° C., to avoid the formation of numerous by-products which were difficult to separate subsequently from the desired product.

Instead of the free acid, it is possible to employ reactants (symmetrical or mixed anhydride or esters) which under the operating conditions liberate the acid whose anilide it is desired to make.

It is a complete surprise that the presence of tungsten carbide, on the one hand, prevents the formation of these by-products and, on the other hand, appears to promote the amidation reaction.

To obtain a satisfactory yield of anilide, it is desirable to employ acid in a stoichiometric excess. There is no upper limit, save an economical one, but it can be mentioned that, in the case of a noncontinuous process, an excess at the beginning of reaction of 0.1 to 4 times, preferably of 0.5 to 3 times the stoichiometric quantity gives a good result; whereas, in the case of a continuous process, an excess which is higher than the lowest of the above values is preferred.

The quantity of water may vary from 0, preferably 10, to 50% by volume of the acid employed.

Another objective of the present invention is to provide a new tungsten carbide-based hydrogenation reaction mixture whose kinetic characteristics are sufficiently improved in comparison to tungsten carbide.

This objective is attained by a reaction mixture characterized in that it comprises:

tungsten carbide treated with hydrogen;

a liquid phase comprising a nitro or nitroso compound as described above; and hydrogen at a pressure of at least approximately 2 atmospheres, advantageously approximately 5 atmospheres, preferably approximately 10 atmospheres.

The following nonlimiting examples illustrate the invention.

In the following examples, the tungsten carbide has a specific surface of approximately 1 $m^2/g$.

Insofar as the partial pressure of hydrogen is concerned, it should be noted that the practice has been to follow the techniques which are conventional in this context, that is to say that the reactor in which the reaction is carried out is connected to a hydrogen bottle by means of a check valve device which controls the pressure in the reactor at the value which is displayed. The partial pressure of hydrogen at the reaction temperature is therefore the displayed pressure minus the autogenous pressure of the reaction mixture.

It should be noted that the present invention is not limited to the use of pure hydrogen; this may be employed in the form of a gas mixture so long as the gases with which it is mixed are substantially inert under the reaction conditions.

Its surprising low sensitivity to sulfur-containing poisons predisposes the reaction mixture according to the invention to the use of gases originating from the gasification of inorganic carbon derivatives such as coals. Water gas, in particular, should be mentioned.

With regard to the yields, the following abbreviations apply:

$$\frac{DC}{\text{(degree of conversion)}} = \frac{Q.S.I. - Q.S.H.}{Q.S.I.}$$

$$\frac{CY}{\text{(yield based on material converted)}} = \frac{Q.D.D.F.}{Q.S.I. - Q.S.R.}$$

$$\frac{RY}{\text{(yield based on material introduced)}} = \frac{Q.D.D.F.}{Q.S.I.}$$

Q.S.I. = Quantity of Substrate Introduced (expressed in moles)
Q.S.R. = Quantity of Substrate Recovered at end of reaction (expressed in moles)
Q.D.D.F = Quantity of Desired Derivative Formed (expressed in moles)

EXAMPLE 1

Hydrogenation of Nitrobenzene 0.5 g of nitrobenzene was introduced into a 35-ml glass bulb and 15 ml of EtOH (ethyl alcohol) and 0.45 g of tungsten carbide was added. The bulb was introduced into a 125-ml stainless steel autoclave. Purging was carried out twice with 10 atmospheres of nitrogen, then twice with 20 atmospheres of hydrogen. A hydrogen pressure of 20 atmospheres was applied and the mixture was heated to 100° C. with agitation. These conditions were maintained for 4 hours. The autoclave was cooled in a water bath. The organic phase was drawn off.

Analysis by gas phase chromatography (GPC) of the product gave a DC of 100% and a selectivity for aniline of 95%.

The catalyst system was recycled without loss of activity.

EXAMPLE 2

Hydrogenation of Nitrobenzene with Bamberger Rearrangement 1.0 g of nitrobenzene and 9 ml of 40% Sulfuric acid were introduced into a 35-ml glass bulb. 0.97 g of tungsten carbide was added. The glass bulb was introduced into a 125-ml autoclave. Purging was carried out twice with 5 atmospheres of nitrogen, then three times with 5 atmospheres of hydrogen.

5 atmospheres of hydrogen were applied. The pressure was kept constant throughout the reaction period. The mixture was heated to 115° C. with agitation. After 5 h and 45 min of reaction, the autoclave was cooled with a water bath. GPC analysis of the reaction mixture after treatment gave a DC of 99.8% and 58% of p-aminophenol.

The catalyst system was recycled without loss of activity.

EXAMPLE 3

Hydrogenation of 3,4-dichloronitrobenzene 10 g of 3,4-dichloronitrobenzene were charged into a 125-ml autoclave and 5.1 g of tungsten carbide and 40 ml of methanol were added.

Purging was carried out twice with 5 atmospheres of nitrogen and twice with 20 atmospheres of hydrogen. Twenty atmospheres of hydrogen were applied and the mixture was heated to 110° C. with agitation. The pressure was kept constant.

After 4 hours' reaction, the autoclave was purged twice with 10 atmospheres of nitrogen after it had cooled. The reaction mixture was filtered.

The DC, which is 100, was determined by GPC (gas phase chromatography) analysis. Its selectivity for 3,4-dichloroaniline was higher than 99%. The presence of chloride, which corresponds to a molar DC not exceeding 0.05%, was detected by polarographic determination.

EXAMPLE 4

Hydrogenation of p-nitrophenol 0.55 g of p-nitrophenol, 15 ml of methanol and 0.45 g of tungsten carbide were introduced into a 35-ml glass bulb.

The glass bulb was introduced into the 125-ml stainless steel autoclave. Purging was carried out twice with 10 atmospheres of nitrogen, then twice with 20 atmospheres of hydrogen. A hydrogen pressure of 20 atmospheres was applied and the mixture was heated to 100° C. while agitating. These conditions were maintained for 4 hours.

Cooling was carried out in a water bath. The organic phase was drawn off and was determined by GPC.

A 59% DC and a 99% selectivity for p-aminophenol were obtained.

The catalyst system was recycled without loss of activity.

EXAMPLE 5

Role of the Solvent in the Hydrogenation of p-nitrophenol 0.55 g of p-nitrophenol and 0.39 g of tungsten carbide were charged into a 30-ml autoclave. 10 ml of water-acetic acid solvent in varying proportions were added.

Purging was carried out twice with 5 atmospheres of nitrogen then twice with 20 atmospheres of hydrogen. A pressure of 20 atmospheres of hydrogen was applied and the mixture was heated to a temperature of 100° C., while agitating and maintaining the pressure at 20 atmospheres. After 4 hours' reaction, the reaction products were analyzed by GPC. The results are given in the table below.

| SOLVENTS | | YIELD OF P-AMINOPHENOL RELATIVE TO PARA-NITROPHENOL (RY) | |
| --- | --- | --- | --- |
| ACOH ml | H$_2$O ml | DC | RY |
| 10 | 0 | 8 | 6% |
| 9 | 1 | 39 | 39% |
| 8 | 2 | 69 | 69% |
| 6 | 4 | 87 | 85% |
| 5 | 5 | 98 | 98% |
| 2 | 8 | 99 | 98% |

EXAMPLE 6

Role of the Solvent in the Hydrogenation

Of p-nitrophenol Using A Palladium-Based Catalyst

This is a comparison example which used a palladium-based catalyst (9 mg 3% Pd/C) but which otherwise employed the conditions of Example 5. The result is:

| SOLVENTS | | YIELD OF P-AMINOPHENOL RELATIVE TO PARA-NITROPHENOL (RY) | |
| --- | --- | --- | --- |
| AcOH ml | H$_2$O ml | DC | RY |
| 10 | 0 | 100% | 54% |

EXAMPLE 7

Reaction in Vapor Phase 5 ml of quartz, 1 ml of tungsten carbide and 5 ml of quartz were introduced into a 20-mm glass reactor. The reactor was heated by an electric oven at 450° C. for 1 hour while the catalyst bed was swept with a stream of hydrogen at 2 liters per hour. The temperature was then reduced to 240° C. and while maintaining a stream of 2 liters per hour of hydrogen, nitrobenzene was introduced at a rate of 0.5 ml per hour with the aid of a syringe drive.

After 3 hours' reaction, GPC analysis gave the degree of conversion (DC) and the real yield (RY) of p-aminophenol were:

DC=48%
RY=39%

EXAMPLE 8

Preparation of Aceto-p-aminophenol (APAP) by Hydrogenation/Acylation Coreaction in Acetic Acid, Catalyzed by Pd/C 7.5 g of p-nitrophenol and 15 ml of an acetic acid-water mixture in the ratio of 80%/20% respectively, by weight, were introduced into a 35-ml glass bulb. 15 mg of 3% Pd/C were introduced. The glass bulb was introduced into a 125-ml autoclave. The autoclave was closed. Purging was carried out twice with 10 atmospheres of nitrogen, then twice with 10 atmospheres of hydrogen.

A pressure of 20 atmospheres was then applied to the autoclave and the mixture was heated to 150° C. with agitation. After the end of hydrogen absorption, the autoclave was cooled to room temperature. The reaction mixture was analyzed by HPLC. The conversion was 17% and the catalyst was poisoned.

EXAMPLE 9

Preparation of APAP by Hydrogenation/Acylation Coreaction in Acetic Acid Catalyzed by Tungsten Carbide 7.5 g of p-nitrophenol, 15 ml of an acetic acid/water mixture containing 80% of acetic acid and 20% of water were introduced into a 35-ml glass bulb. 3 g of tungsten carbide were introduced. The glass bulb was introduced into a 125-ml autoclave. The latter was closed and purged twice with 10 atmospheres of nitrogen, then twice with 10 atmospheres of hydrogen. The autoclave was then placed under 20 atmospheres of hydrogen and heated to 150° C. with agitation. The autoclave pressure was maintained at 20 atmospheres throughout the reaction period.

After the hydrogen absorption ended, the autoclave was cooled to room temperature. The conversion was complete and 99.5% of APAP was determined by HPLC. The tungsten carbide was recycled without loss of activity.

EXAMPLE 10

Hydrogenation of 5-Chloro-2-fluoronitrobenzene 10 g of 5-chloro-2-fluoronitrobenzene and 10 ml of water-methanol mixture in the ratio ⅔ were introduced into a 35-ml glass bulb. 2.5 g of tungsten carbide were then introduced. The glass bulb was charged into a 125-ml autoclave. The latter was purged twice with 10 atmospheres of nitrogen, then twice with 10 atmospheres of hydrogen. The reactor was then placed under 20 atmospheres of hydrogen, agitated and heated to 120° C. The pressure of 10 atmospheres in the autoclave was maintained throughout the reaction period. After 4 hours' reaction, the hydrogen consumption ceased.

These conditions were further maintained for 1 hour. GPC analysis showed that the conversion was complete and that the yield of 5-chloro-2-fluoroaniline was higher than 99.8%. The hydrodehalogenation was lower than 0.2%, measured by ionometry.

EXAMPLE 11

Hydrogenation of 2,3-dichloronitrobenzene 10 g of 2,3-dichloronitrobenzene and 10 ml of a water/methanol mixture in the ratio ⅔ were introduced into a 35-ml glass bulb. 2.5 g of tungsten carbide were added. The glass bulb was introduced into a 125-ml autoclave. The autoclave was closed and purged twice with 10 atmospheres of nitrogen, then twice with 10 atmospheres of hydrogen. The autoclave was then placed under 20 atmospheres of hydrogen and heated to 120° C. with agitation. The pressure of 20 atmospheres was maintained in the autoclave.

After 3 hours' reaction, the hydrogen consumption ceased. These temperature and pressure conditions were further maintained for 1 hour. By GPC determination it was shown that the conversion was complete and the yield of 2,3-dichloroaniline was higher than 99.5%. The hydrodechlorination was lower than 0.2%. The catalyst was recycled without loss of activity.

EXAMPLE 12

Hydrogenation/Acylation of 3-chloro-4-fluoronitrobenzene in Acetic Acid 10 g of 3-chloro-4-fluoronitrobenzene and 10 ml of a 90/10 by weight acetic acid/water mixture were introduced into a 35-ml glass bulb. 2.5 g. of tungsten carbide were added. The glass bulb was introduced into a 125-ml autoclave.

The latter was closed and purged twice with 10 atmospheres of $N_2$ and then twice with 10 atmospheres of hydrogen. The autoclave was then placed under 30 atmospheres of hydrogen and heated to 150° C. with agitation. The hydrogen pressure was maintained at 20 atmospheres throughout the reaction period.

After the hydrogen absorption has ended, cooling was applied.

The conversion was complete and the yield of 3-chloro-4-fluoroacetanilide was 97%.

EXAMPLE 13

Hydrogenation/Acylation of 3,4-dichloronitrobenzene in Acetic Acid 10 g of 3,4-dichloronitrobenzene and 10 ml of a 90/10 by weight acetic acid/water mixture were introduced into a 35-ml glass bulb. 2.5 g of tungsten carbide were added.

The glass bulb was introduced into a 125-ml autoclave. The latter was closed and purged twice with 10 atmospheres of nitrogen, then twice with 10 atmospheres of hydrogen.

The autoclave was then placed under 20 atmospheres of hydrogen and heated to 150° C. with agitation. The autoclave pressure was maintained at 20 atmospheres throughout the reaction period.

After the hydrogen absorption ended, cooling was applied. The conversion was complete and the yield of N-acetyl-3,4-dichloroaniline was 98%.

EXAMPLE 14

Hydrogenation of 2,4-dinitrotoluene in a semicontinuous process 200 ml of water and 2.5 gram of tungsten carbide were introduced into a 750 ml SOTOLEM™ reactor. The glass bulb reactor was introduced into a 125 ml. closed autoclave. The reactor was purged twice with 10 atmospheres of nitrogen and twice with 10 atmospheres of hydrogen. 20 atmospheres of hydrogen were charged to the autoclave and the pressure quickly rose to 90 atmospheres when the mixture was heated to 185° C. with agitation. Over a period of 70 minutes, a solution of 26 grams of 2,4-dinitrotoluene and 100 ml of diglyme was injected. The total pressure was maintained at 90 atmospheres for the duration of the reaction. The consumption of hydrogen was measured by pressure difference in a reservoir of known volume. Immediately following the end of the injection of the 2,4-dinitrotoluene, the consumption of hydrogen stopped. Gas chromatography of the reaction medium showed that the DC was 100% and the yield based on the material converted (RY) was 99% 2,4-diaminotoluene.

What is claimed:

1. A reagent for hydrogenation of a nitroaromatic compound or a nitrosoaromatic compound, comprising
   (a) a tungsten carbide catalyst prepared by subjecting tungsten carbide, or a composite containing tungsten carbide, in liquid medium to hydrogenation at a temperature and pressure selected from the group consisting of (i) a temperature of at a temperature of at least 100° C. at a pressure of at least 10 atmospheres, and (iii) a temperature of at least 150° C. at a pressure of at least 2 atmospheres;
   (b) hydrogen at a pressure of at least 2 atmospheres; and
   (c) a liquid phase.

2. A reagent according to claim 1 wherein the hydrogenation treatment of the catalyst takes place in a liquid medium at a temperature of at least 100° C., and at a pressure of at least 10 atmospheres.

3. A reagent according to claim 1 wherein the catalyst has a specific surface from 0.1 to 1000 square meters per gram.

4. A reagent according to claim 3 wherein the specific surface of the catalyst is from 1 to 500 square meters per gram.

5. A reagent] according to claim 2 wherein the catalyst has a specific surface from 0.1 to 1000 square meters per gram.

6. A reagent according to claim 5 wherein the specific surface of the catalyst is from 1 to 500 square meters per gram.

* * * * *

UNITED STATES PATENT AND TRADEMARK OFFICE
CERTIFICATE OF CORRECTION

PATENT NO. : 5,646,085
DATED : July 08, 1997
INVENTOR(S) : Roland JACQUOT et al.

It is certified that error appears in the above-indentified patent and that said Letters Patent is hereby corrected as shown below:

Claim 1, column 13, line 17, after "temperature of at" (first occurrence), insert --least 60°C at a pressure of at least 20 atmospheres, (ii)--.

Claim 5, column 14, line 13, after "reagent", delete "]".

Signed and Sealed this

Fifth Day of May, 1998

Attest:

BRUCE LEHMAN

*Attesting Officer*   *Commissioner of Patents and Trademarks*